(12) United States Patent
Zelener et al.

(10) Patent No.: US 7,211,113 B2
(45) Date of Patent: May 1, 2007

(54) HIP PROSTHESIS

(76) Inventors: Lev Zelener, 2263 64 St., #B6, Brooklyn, NY (US) 11204; Konstantin Sherepo, 21 Matros Zheleznyak Boulvare, #89, Moscow (RU) 125239; Marina Zelener, 240 Ocean Pkwy., #2 C, Brooklyn, NY (US) 11218; Anton Svetlanov, 43-70 Kissena Blwr., #21 H, Brooklyn, NY (US) 11355

( * ) Notice: Subject to any disclaimer, the term of this patent is extended or adjusted under 35 U.S.C. 154(b) by 484 days.

(21) Appl. No.: 10/848,799

(22) Filed: May 18, 2004

(65) Prior Publication Data

US 2005/0261778 A1 Nov. 24, 2005

(51) Int. Cl.
*A61F 2/30* (2006.01)
*A61F 2/32* (2006.01)
*A61F 2/36* (2006.01)
*A61F 2/34* (2006.01)

(52) U.S. Cl. ............................... 623/22.43; 623/22.46; 623/23.17; 623/23.19; 623/23.23; 623/23.26; 623/23.3; 623/23.37; 623/23.46

(58) Field of Classification Search ............... 623/22.4, 623/22.42, 22.43, 22.44, 22.45, 22.46, 23.13, 623/23.14, 23.15, 23.17, 23.18, 23.19, 23.2, 623/23.21, 23.22, 23.23, 23.24, 23.25, 23.26, 623/23.27, 23.28, 23.29, 23.3, 23.31, 23.32, 623/23.33, 23.34, 23.35, 23.36, 23.37, 23.38, 623/23.44, 23.46, 23.11, 23.12
See application file for complete search history.

(56) References Cited

U.S. PATENT DOCUMENTS

| | | | |
|---|---|---|---|
| 4,159,544 A | 7/1979 | Termanini | |
| 4,770,661 A | 9/1988 | Oh | |
| 5,021,063 A | * 6/1991 | Tager | 623/23.33 |
| 5,389,107 A | * 2/1995 | Nassar et al. | 623/23.17 |

(Continued)

FOREIGN PATENT DOCUMENTS

RU 2223068 2/2004

(Continued)

OTHER PUBLICATIONS

Lev Zelener "Modern Hip Joint Replacement" Oct. 15, 2004, http//www.hipjoint.blogspot.com INTERNET.

(Continued)

*Primary Examiner*—Corrine McDermott
*Assistant Examiner*—Thomas J Sweet
(74) *Attorney, Agent, or Firm*—Yefim Kreydin (57) ABSTRACT

An endoprosthesis utilizes a biomechanical structure based on the lever model of first degree. Contrary to the widespread practice, the inventive structure has a stem placed inside the femur bone, which is not rigidly attached to this bone. Accordingly, the bone, following its known tendency to slightly pivot away from the medial plane of the body in response to the loads, does not directly contact the stem. The neck portion experiences even greater loads then the stem. The supporting anchor has a region extending laterally from the stem and pressing against a supporting surface of the housing, which also extends laterally from the body of the housing. Since the stem, supporting anchor and neck are typically constitute a one-piece component, the lateral surfaces of the supporting anchor and housing are in continuous frictional contact during displacement of the stem and housing relative to one another.

17 Claims, 5 Drawing Sheets

U.S. PATENT DOCUMENTS

| | | | | |
|---|---|---|---|---|
| 5,571,203 | A * | 11/1996 | Masini | 623/22.46 |
| 5,725,597 | A * | 3/1998 | Hwang | 623/22.15 |
| 5,876,459 | A * | 3/1999 | Powell | 623/23.15 |
| 5,906,644 | A * | 5/1999 | Powell | 623/20.15 |
| 6,085,476 | A * | 7/2000 | Jantzi et al. | 52/223.7 |
| 6,302,913 | B1 * | 10/2001 | Ripamonti et al. | 623/16.11 |
| 6,355,068 | B1 * | 3/2002 | Doubler et al. | 623/22.42 |
| 6,425,922 | B1 | 7/2002 | Pope | |
| 6,488,716 | B1 * | 12/2002 | Huang et al. | 623/23.12 |
| 6,682,568 | B2 * | 1/2004 | Despres et al. | 623/22.42 |
| 6,692,530 | B2 * | 2/2004 | Doubler et al. | 623/22.42 |
| 6,899,736 | B1 * | 5/2005 | Rauscher et al. | 623/19.12 |
| 7,033,399 | B2 * | 4/2006 | Doubler et al. | 623/22.42 |
| 7,044,975 | B2 * | 5/2006 | Cheal et al. | 623/22.42 |
| 7,097,664 | B2 * | 8/2006 | Despres et al. | 623/22.42 |
| 2001/0014829 | A1 * | 8/2001 | Yoon | 623/23.46 |
| 2002/0004685 | A1 * | 1/2002 | White | 623/23.15 |
| 2003/0074078 | A1 * | 4/2003 | Doubler et al. | 623/22.42 |
| 2003/0171816 | A1 * | 9/2003 | Scifert et al. | 623/22.12 |
| 2004/0054419 | A1 * | 3/2004 | Serra et al. | 623/22.42 |
| 2004/0107001 | A1 * | 6/2004 | Cheal et al. | 623/22.42 |
| 2004/0243248 | A1 * | 12/2004 | Despres et al. | 623/22.42 |
| 2006/0064169 | A1 * | 3/2006 | Ferree | 623/17.12 |

FOREIGN PATENT DOCUMENTS

SU     1572604     12/1987

OTHER PUBLICATIONS

Ed. Kondrashin "Guide to Prostheses" 1988, pp. 87, 88, Medicine, Moscow USSR.

* cited by examiner (Prior Art)

HIP PROSTHESIS

BACKGROUND OF THE INVENTION

Replacement devices such as artificial joints in general and especially those for the hip have been known for many years. Such replacement devices include substitute members for the two parts of the natural joint, namely the femoral head, which is joined to the femur, and the hip socket, which receives and cooperates with the head to provide a natural universal joint.

Replacement of the natural hip joint parts is necessary when deterioration has occurred to one or both of the natural femoral head and socket. Ideally, the replacement members should reproduce the structure and function of the original members. For example, it is important that the femoral head be securely attached to the femur, that the head be received within the socket and that the resulting joint be produced with the desirable degree of resilience or cushioning.

All known prior art, for example U.S. Pat. No. 4,770,661 and U.S. Pat. No. 4,159,544 disclose a system associated with resorption of bone tissue, protrusion of the bottom of acetabulum, and loosening of the stem due to a relatively high pressure upon the bone. Furthermore, localized pressure generated by the prosthesis parts causes greater than naturally occurring displacement of the stem from its initial position. Particularly, in the upper part, the stem tends to move medially, while in the lower part, it moves outwardly laterally.

Currently used endoprosthesis models typically take into consideration the biomechanics of the femur, which is rather similar to a console. This view is applied both to normal hip joints and total joint replacements and is usually realized by a system configured to rigidly fix the stem of endoprosthesis to the surrounding bone. Typically, to further this goal, the stem may have various geometrical forms for compressive fixation; alternatively or in addition to the specifically designed forms, it is not uncommon to cement the stem to the bone.

The clinical practice and numerous data show that this approach may not fully take into consideration the following:
  even after milling of the channel through the femur diaphysis, the femur bone still contains a live tissue requiring circulation of tissue fluid, which may be detrimentally affected by cementing, and
  during walking, the femur bone rotates around its long axis thus gradually weakening a bond between this bone and the prosthesis. (See *Guide to prosthetics*, N. Kondrashin, Moscow, "Medicine" 1988, pages 87,88).

SUMMARY OF THE INVENTION

Thus, a primary object of the present invention is to improve the stability of hip joint endoprosthesis.

A further object of the present invention is to substantially reduce and eventually to completely eliminate complications associated with at least some of the currently used endoprosthesis models.

Still a further object is to provide the recipients of the inventive hip joint endoprosthesis with a fully functional life.

To achieve these objects, an endoprosthesis configured in accordance with the invention utilizes a biomechanical structure based on the lever model of first degree. In other words, contrary to the widespread practice of cementing the entire endoprosthesis to the femur bone, the inventive structure has at least one component, a stem placed inside the femur bone, which is not rigidly attached to this bone. Accordingly, the bone, following its known tendency to slightly pivot away from the medial plane of the body in response to the loads, does not directly contact the stem.

As a consequence, while in the known prior art structures, such a direct contact would rather rapidly wear out the bond between the housing and stem, the inventive structure avoids such a drawback exhibiting a long functional life.

Yet the ability of the inventive structure to withstand numerous loads is not compromised due an elongated outer housing extending beyond the distal (lower) end of the stem and reliably coupled to the bone. Such a coupling is ensured by a plurality of holes formed in the outer housing and allowing bone tissue to penetrate through the holes and bond with the outer housing. Furthermore, the holes provide for the circulation of the tissue fluid indispensable for maintaining the ingrown tissue.

In accordance with a further aspect of the invention, the endoprosthesis includes a sleeve made from porous material and located between the stem and outer housing. Accordingly, the sleeve reduces the friction during rotation of the stem and outer housing relative to one another, which in turn minimizes formation of granules typically originated during such a friction and known to weaken the bone. Material of the sleeve also plays an important role in maintaining the circulation of the tissue fluids within the inventive prosthesis.

Still another aspect of the invention is directed to further minimizing frictional forces between the neck portion of the stem, which extends angularly from the stem towards the bone's head, and the housing. Formed with a supporting anchor and a neck inserted into the head of femur, the neck portion experiences even greater loads then the stem. In particular, the supporting anchor has a region extending laterally from the stem and pressing against a supporting surface of the housing, which also extends laterally from the body of the housing. Since the stem, supporting anchor and neck typically constitute a one-piece component, the lateral surfaces of the supporting anchor and housing are in continuous frictional contact during the movement of the stem and housing relative to one another. To minimize deterioration of these surfaces, the inventive structure includes at least one plate inserted into one of the lateral surfaces of the supporting anchor and housing. Said at least one plate made of material with a low friction coefficient.

The above and other objects, features and advantages of the present invention will become more clearly understood from the following description referring to the accompanying drawings.

DESCRIPTION OF THE PREFERRED EMBODIMENTS

Figure 1:
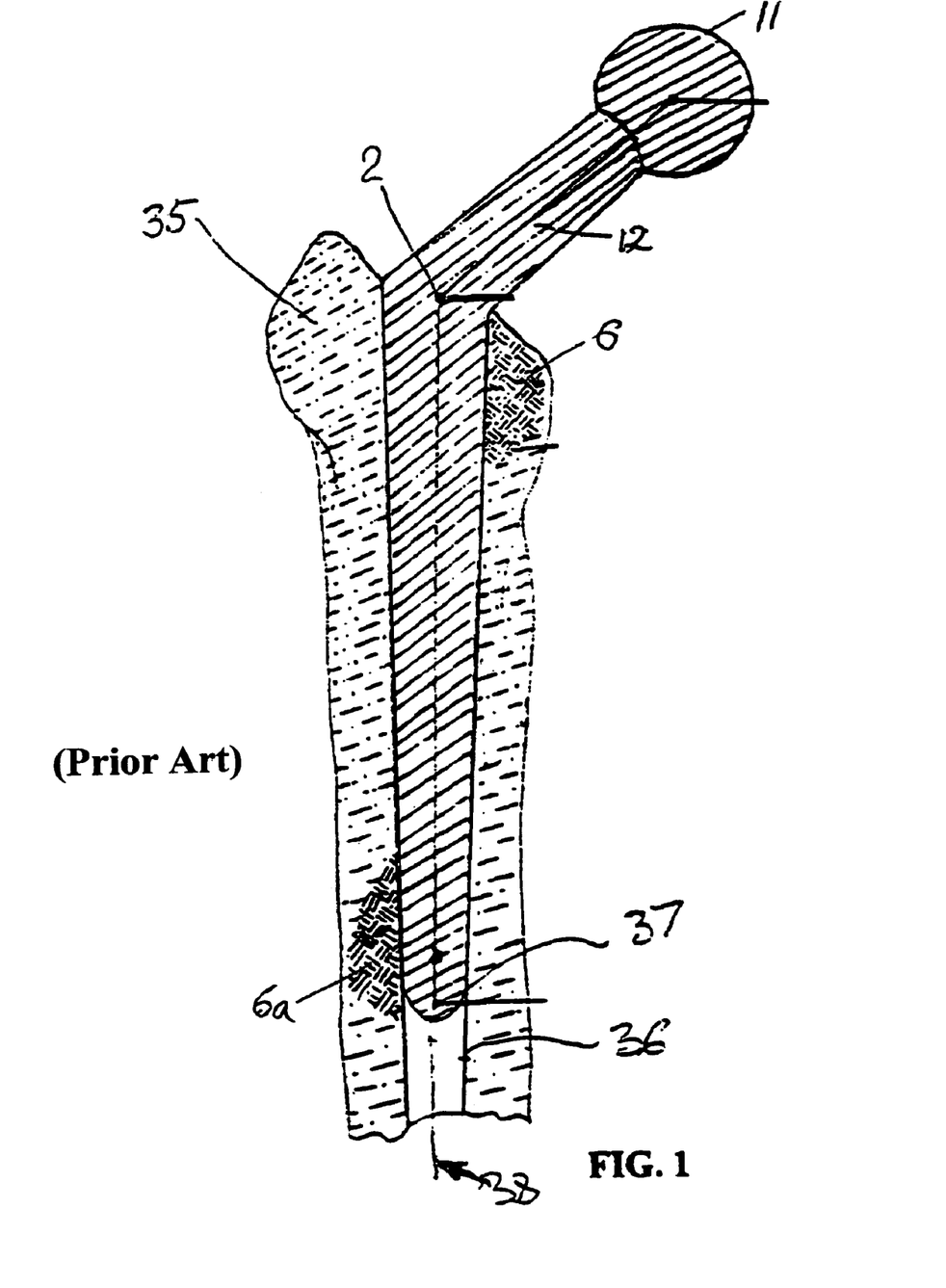
FIG. 1 is a schematic representation of biomechanics of the femur with total joint replacement.
Figure 2:
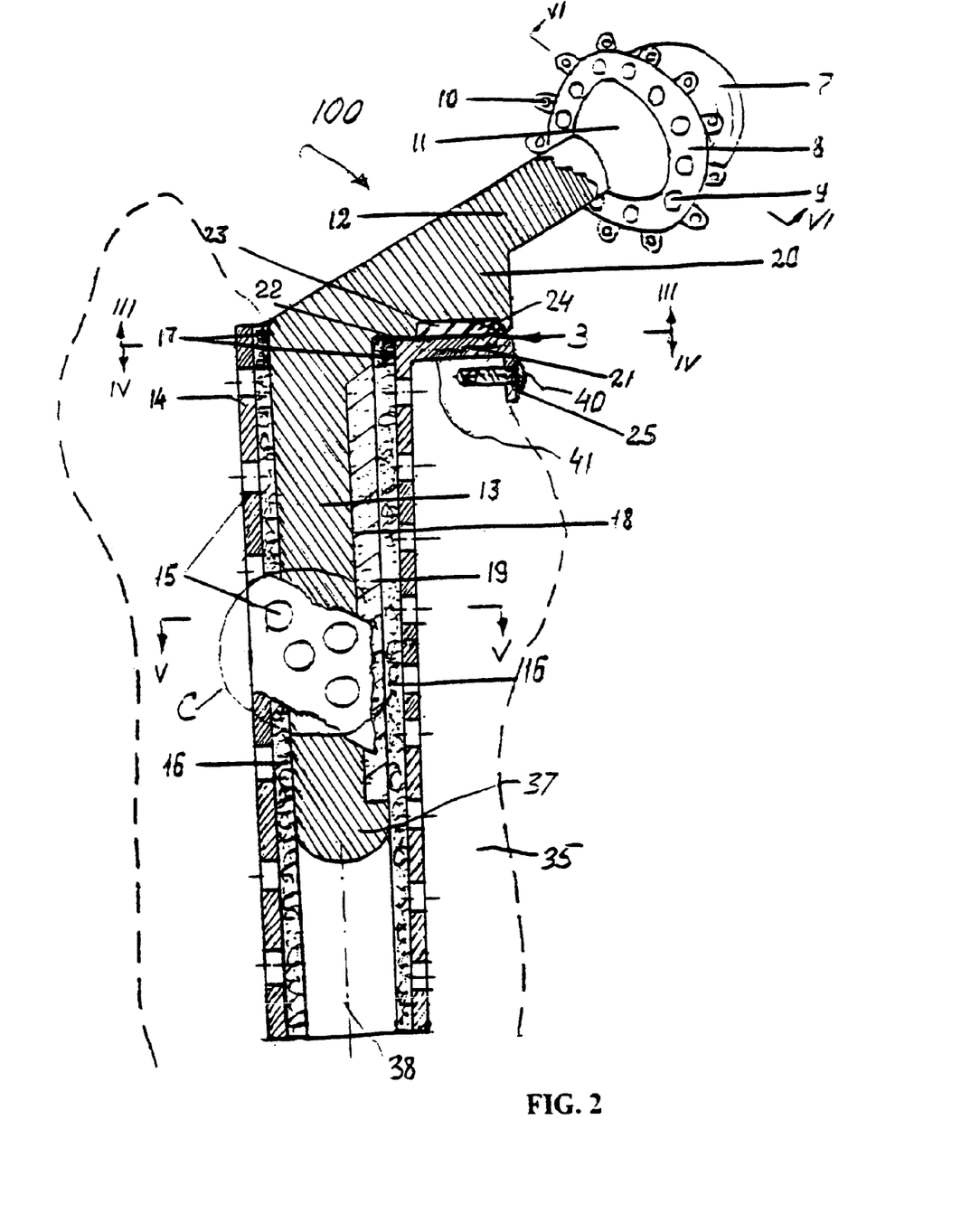
FIG. 2 is a longitudinal partially sectional view of the inventive endoprosthesis.

Referring to FIGS. 1–2, the anatomical structure of the hip joint includes the femur diaphysis, further referred to as a bone 35, neck and head 11. If a situation requires the hip replacement, it is performed by removing the neck, forming a channel 36 within the bone 35 and introducing a stem 13 (FIG. 2) of a prosthesis 100 into the channel 36. Formed integrally with the stem 13 is a neck portion 12 of the prosthesis 100, which extends angularly from the stem 13 into a cup 7 that is attached to the head of the bone.

As follows from the clinical practice, loading of the prosthesis cup leads to the greatest bone resorption of the femur diaphysis in its upper medial part 34, as this is where the most of the body weight load is applied. The prosthesis stem 13 and particularly its distal end 37, are pushed laterally away form the median plane 39 (FIG. 4), as shown by an arrow "38" in FIG. 1 due to the inherent motion of the bone 35 occurring as a result of applied loads.

If the prosthesis were constructed in accordance with the convenient practice as a console model, displacement of the bone 35 would gradually destroy cement typically bonding the stem and bone 35. In contrast, the inventive prosthesis 100 is configured as a lever of the first kind with an axis 2 of the lever characterized by a substantial degree of freedom between the stem 13 and the bone 35. As a result, the bone 35 is free to follow its natural pattern of rotation, and the bond between a housing 14 of the prosthesis 100 and the bone 35 is not affected.

The pressure by the prosthesis stem 13 on the lateral side of the femur diaphysis channel is increased by the physiological abduction of the femur bone (incline to the medial), equal 8 degrees relative to the vertical body axis.

Placement of the endoprothesis 100 into the bone 35 is realized by severing its neck along a plane extending substantially perpendicular to the medial plane MP. Of course, small deviations from the perfectly perpendicular plane ranging within a few degrees would not drastically reduce the effectiveness of the prosthesis. To completely remove the damaged hip joint, the cup of the bone is removed from the bone's head. As a result, upon milling the channel 36 for the stem 13 (FIGS. 1, 2), the housing 14 and stem 13 are introduced into the channel 36, while the neck portion 12 of the prosthesis 100 terminates in the bone's head 11 in accordance with the normal course of the standard operation disclosed in detail below.

Figure 2A:
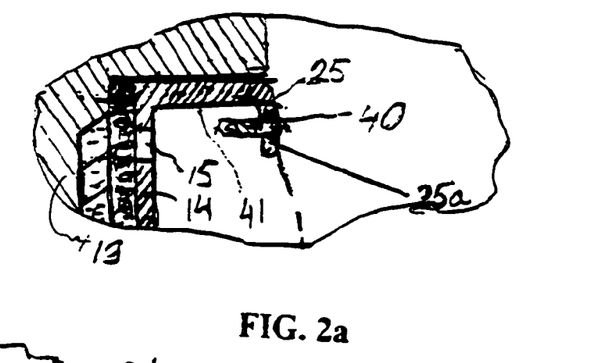
FIG. 2a is a longitudinal partially sectional view of an embodiment of the FIG. 2.

Rigidly coupling the cup 7 to the bone 35's head while coupling the housing 14 to the bone 35 completes the replacement procedure. Coupling the housing 14 to the bone 35 is realized by the inventive configuration of the housing 14 provided with a plurality of holes 15, 151 (FIGS. 2, 2a, 2c) allowing the bone 35 tissue to ingrow and absorb within the housing 14. The number of these holes and their shape is arbitrary, but, based on experimental data and individual anatomy of the recipient, may be limited to 16–18 holes, preferable elliptical (151) each having dimensions of about 2–3 to 4–6 mm or round (15) each having a diameter of about 3–4 mm, patterned spirally or in staggered arrangement around the circumference of the housing 14. Preferably, the housing 14 has an annular periphery narrowing towards its distal end. The material the housing 14 is made preferably from Titanium or Titanium alloys. Advantageously, the housing 14 is manufactured from biologically friendly material including, but not limited to, various metals as stainless steel, Tantalum.

A flange 21 of the housing 14 (FIGS. 2 and 2a) extends corolla-like along the whole length of the substantially horizontal section 41 of the bone 35 (the bone is displayed as a dotted line on FIG. 2) from one side of the greater trochanter to the other. A rim 25 with blades 25a formed on and extending transversely to the flange 21 along the lateral side of the bone 35 and receives screws 40 (FIGS. 2, 2A) penetrating the adjoining portion of the bone 35. The number of screws 40 is not limited and may be increased by inserting multiple screws at the appropriate locations selected by the operating surgeon. In tern, the housing 14 and the bone 35 are reliably coupled to synchronously pivot about an axis 38 (this axis extends substantially along the central portion of the stem 13) extending parallel to the median plane 39 (FIG. 4) Ability of the housing 14 to withstand linear loads generated by the recipient of the prosthesis 100 is provided by the reliable material preferably Titanium or Titanium alloys. Advantageously, the housing 14 is manufactured from biologically friendly material including, but not limited to, various metals as stainless steel, Tantalum, and preferably has an optimal wall thickness of up to about 0.3–0.5 mm.

The diameter of the stem 13 is dimensioned somewhat smaller than the inner surface of the housing 14 to prevent direct contact between these components of the prosthesis 100. When the cup 7 is rigidly coupled to the bone 35's head, displacement of the stem 13 does not directly affect displacement of the housing 14 pivoting along with the bone 35. Accordingly, these components pivot independently from one another in a rather natural manner.

To reinforce the stem/housing combination, the prosthesis 100 further includes a sleeve 16 (FIGS. 2, 2a) coextending with the housing 14 and wrapping the outer periphery of the stem 13. Mutual displacement of the stem 13 and the housing 14 may cause undesirable displacement of the distal end 37 (FIG. 2) of the stem 13. Dimensioning the housing 14 and the sleeve 16 so that both of these elements project beyond the distal end of the stem 13 at about 15–20 mm allows these components to minimize the stem's pressure on the bone 35 thereby protecting this bone 35 and precluding the formation of granulations 6a (FIG. 1).

The proximal end of the sleeve 16 is provided with a collar 17 abutting a lower portion of the stem 13 near a heel 22 to ensure proper positioning of the sleeve within the housing 14.

The collar 17 made from Teflon™ (polytetrafluoroethylene) and the sleeve 16 is made of Teflon fabric, for example from medical felt from ftoroplast 4" (produced with this name in Russia) and having porous structure. The sleeve 16 is not affected by the ingrown tissue and is resistant to tissue fluid that is normally is secreted. Most importantly, the sleeve 16, having a thickness of about 1–1.5 mm, has a low friction coefficient and does not greatly inhibit the movement of the housing 14.

Figure 2B:
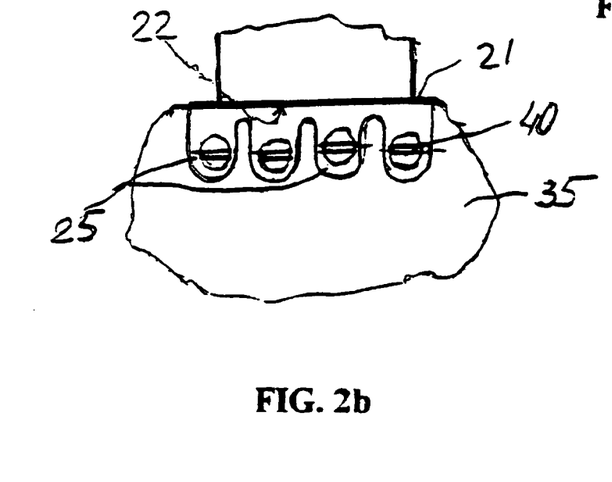
FIG. 2b is a partial view from arrow B of the FIG. 2.
Figure 3:
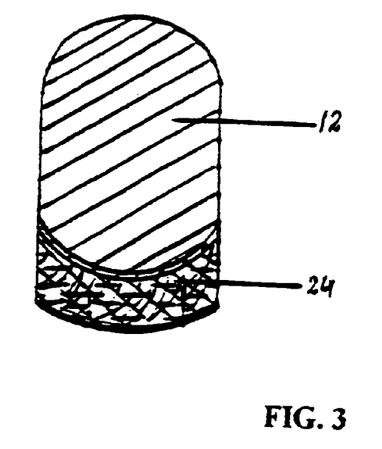
FIG. 3 is a schematic view of a supporting anchor seen from arrows III—III of the FIG. 2.
Figure 4:
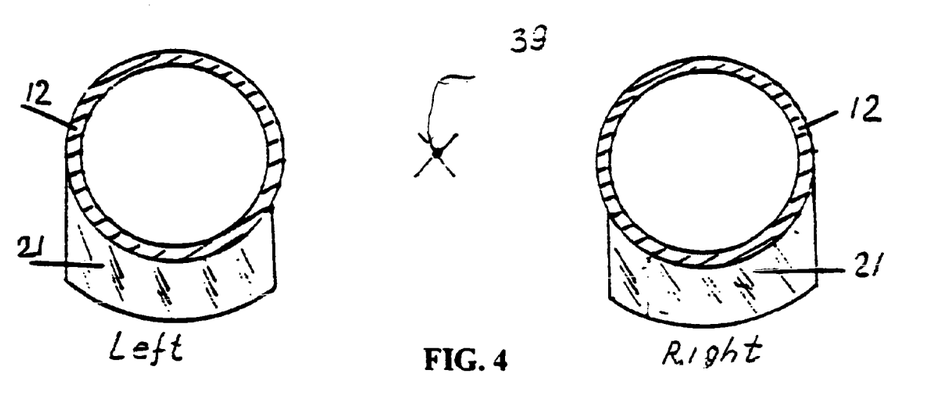
FIG. 4 is a schematic view of a supporting rim of the metal casing seen from arrows IV—IV of the FIG. 2.

The neck portion 12 of the prosthesis 100 (FIG. 2) terminates in the cup 7, whereas its lower portion 20 supports the stem 13 and has heel 22 extending substantially along the entire length of the housing's flange 21. The sizes and the area of the housing's flange 21 exceed the sizes of the heel 22 (FIGS. 2B, 3 and 4), and a configuration of support flange 21 for the prosthesis 100 for the left and right leg do not coincide. It is due to that the bone 35 and the housing 14 connected to it tend a turn in external concerning the plane 39. Therefore the border of the support flange 21 from internal side to the plane 39 can be less then the diameter of the housing 14 (FIGS. 2B and 4).

Figure 2C:
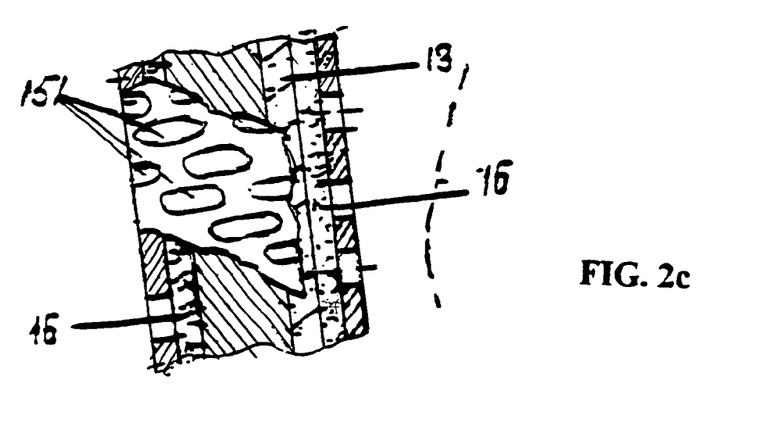
FIG. 2c is a partial sectional view of the region C of an embodiment of the FIG. 2.

As a consequence, unless dealt with, the contact region between the flange 21 and the heel 22 of the lower portion 20 have the opposing surfaces of the flange 21 and heel 22 extended substantially perpendicular to the longitudinal body of the housing 14 may inhibit the independent rotation of the stem 13 and the housing 14 relative to one another. To minimize this unavoidable friction, at least one of the juxtaposed surfaces of these components has spaced recesses 23 (FIG. 2) each receiving a respective insert 24 The recesses 23 each are dimensioned to have a diameter substantially equal to the diameter of the heel 22 of the lower portion 20 and a depth of about 5–8 mm and a length of about 5–7 mm corresponding to the dimension of the insert 24. The latter is made from low friction material such as Teflon or Kynar™ (Fluorine containing Synthetic Resin) and fixed to the heel 22 by any of conventional methods, for example by adhesive or by screws (not shown in the drawings) and has a height up to 1 mm more then depth of the recesses 23. While the opposing surface, for example the surface of the flange 21, as shown in FIGS. 2, 2b, 2c can also be recessed to receive similar or other implants, it is preferred that this surface would be simply polished or covered by material with a low friction coefficient such as polycrystalline diamond as describe in U.S. Pat. No. 6,425,922 which is incorporated herein by reference. Overall, the place between the heel 22 with the insert 24 and the surface of the flange 21, said surface are polished or covered by material with a low friction coefficient, is the place of support of the axis 2 of the levers as the lever of the first kind with maximum loading on the given area of the bone 35 this support area reduced the possibility of granulations 6 and due to a good sliding action between the housing 14 and the sleeve 16, between the heel 22 with the insert 24 and the polished or covered by material with a low friction coefficient surface of the flange 21, the stem 13 of the endoprosthesis 100 can rotate slightly during walking without causing rotational stress to the femur diaphysis, thereby protecting this bone 35 and precluding the formation of granulations 6. It enables to apply the endoprosthesis according the present invention at the situation requires the second hip replacement when the bone 35 is weakened or damaged by use of conventional endoprosthesis during the first hip replacement.

Figure 6:
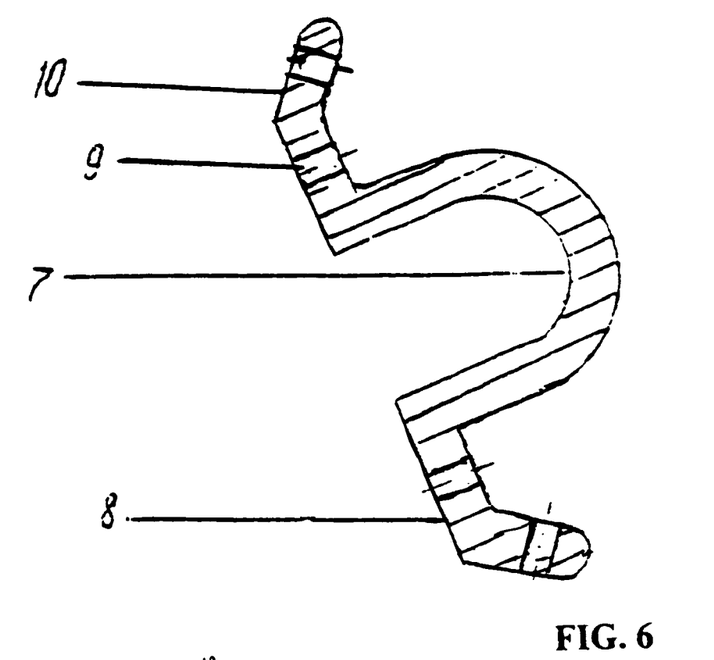
FIG. 6 is a longitudinal sectional view of the inventive cup (sectional view VI—VI of the FIG. 2).

The endoprosthesis cup 7 (FIGS. 2 and 6) has a supporting crown 8 lying on the whole cortical arc of the acetabulum and on the pubic bone 35 with its lower part. The supporting crown 8 has a plurality of holes 9, for example 6–8 holes each dimensioned to have a diameter of about 3–4 mm for tissue fluid filtration, and 9–12 blades 10 with holes dimensioned to be traversed by medical screws. Thus, prosthesis cup 7 is precluded from protrusion through the acetabulum and from displacing during body movements.

The stem 13 and the neck portion 12 define a one-piece component made preferably from Titanium or Titanium alloys. Advantageously, the housing 14 is manufactured from biologically friendly material including, but not limited to, various metals as stainless steel, Tantalum.

Figure 5:
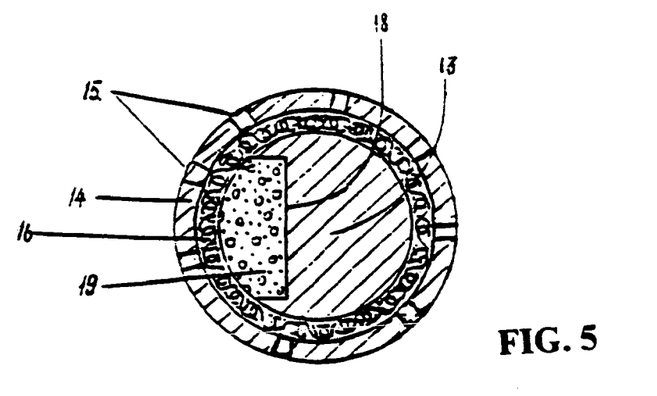
FIG. 5 is a cross-sectional view V—V of the FIG. 2.

The endoprosthesis stem 13 is subjected to the lesser load from the medial then from the lateral side. This created an opportunity of making a trough 18 (FIGS. 2 and 5) with the depth of no more then ⅓ of the stem's diameter, and with the outside circumference length of about ⅓ of the stem (120°). The trough starts at about 10 mm below the joining of the stem 13 with the neck 12 of the endoprosthesis, and ends at about 10 mm above the stem's distal end 37. The bottom 18 of the trough 13 is preferably rectangular in its transverse section and filled with bone 35-replacing mass 19 of bioactive material including, but not limited to calcium phosphates—calcium phosphate ceramics (hydroxyapatite). This and similar materials are suffused with one of numerous modern antibiotics to create an antibacterial environment throughout the diaphysis channel receiving the stem 13 and the housing 14. Bone 35 ceramics is placed in the area of the smallest load on the stem, wrapped by the porous sleeve 16 and is not subjected to mechanical stress.

The surgery directed to the installlation of the endoprosthesis 100 is performed regularly. After accessing the hip joint, transverse osteotomy of the neck 12 and the head 11, of the femur is performed, moving to the base of the greater trochanter, but not including the great trochanter itself. The acetabulum and the femoral channel are milled, the prosthesis cup is inserted into the acetabulum, pressing the crown 8 of the cup tightly and fixing it with surgical screws through the blades 10 to fix the cup 7 tightly and support it by the outside edges of the acetabulum. The metal housing 14 is inserted into the femoral channel. The stem 13, wrapped into the teflon sleeve 16 is inserted into the casing 14 in such a way that the anchor support 20 of the neck 12 rests on the polished surface 25 of the casing rim 14. Manipulating the patient's extremity, the head of the prosthesis is inserted into the cup 7. This ends the technical part of the hip replacement procedure.

Hemostasis is performed, the drainage is created, and muscles are reattached (depending on the technique), wound closure is performed. This ends total hip replacement procedure.

Having described the preferred embodiments of the invention by referring to the accompanying drawings, it should be understood that present invention is not limited to this precise embodiment but various changes and modifications thereof could be made by one skilled in the art without departing from the spirit or scope of the invention as defined in the appended claims.

What is claimed is:

1. An endoprosthesis for replacing a hip joint, comprising:
a stem adapted for insertion into a femur medullar cavity,
a neck extending from the stem and terminating with a head of the endoprosthesis;
said head inserted into an endoprosthesis cup;
said cup adapted for fixation in an acetabulum;
a housing adapted to be received within a bone and configured to surround the stem, so that the housing and the stem are spaced apart to permit rotation of the housing together with the femur around the stem;
a flange extending laterally from one side of the housing,
a heel extending laterally from one side of the neck, wherein
the housing has a longitudinal body and the flange adapted to sit atop the bone to support the heel of the neck portion thereby minimizing loads upon the stem.

2. The endoprosthesis of claim 1, wherein the flange of the housing and the heel of the neck portion have opposing surfaces, at least one of the opposing surfaces being provided with a recess receiving a respective insert frictionally pressing upon the other opposing surface during rotation of the stem and housing relative to one another.

3. The endoprosthesis of claim 2, wherein the opposing surfaces of the flange and heel extend substantially perpendicular to the longitudinal body of the housing.

4. The endoprosthesis of claim 3, wherein the surface of the flange of the housing is polished, the surface of the heel opposing the polished surface of the flange being provided with at least one recess receiving the respective insert, the insert being made of material providing insignificant friction between the opposing surface during the relative rotation of the stem and housing.

5. The endoprosthethis of claim 4, wherein the material of the insert is polytetrafluoroethylene.

6. The endoprosthesis of claim 2, wherein the opposing surfaces of the flange and the heel are oval shaped, the flange has a polished supporting surface and the supporting polished surface of the flange being longer on its medial side and the surface of the heel being longer on its lateral side.

7. The endoprosthesis of claim 4, wherein the surface of the rim of the housing is provided with a layer of low friction material.

8. The endoprosthesis of claim 1, wherein the housing extends beyond a distal end of the stem spaced from the neck portion to minimize stresses upon the bone produced by the stem.

9. The endoprosthesis of claim 8, wherein the housing is about 10–15% longer then the stem.

10. The endoprosthesis of claim 1, wherein the housing has a periphery provided with a plurality of throughgoing holes configured to allow bone tissue to grow through the holes into an interior of the housing so as to ensure a bond between the housing and the bone and tissue fluid to circulate through the ingrown tissue.

11. The endoprosthesis of claim 10, wherein the plurality of throughgoing holes form a spiral pattern along the periphery of the housing and each have elliptical shape.

12. The endoprosthesis of claim 9, wherein the plurality of throughgoing holes form in staggered arrangement along the peripheiy of the housing and each have an elliptical shape.

13. The endoprosthesis of claim 1, further comprising a sleeve coextending with the housing beyond a distal end of the stem and tightly wrapping the stem, the sleeve being made from porous material of polytetrafluoroethylene.

14. The endoprosthesis of claim 13, wherein the sleeve has a collar pressing against a lower portion of the neck portion to prevent displacement of the sleeve.

15. The endoprosthesis of claim 12, wherein the stem being provided with a trough extending substantially along an entire length of the stem and juxtaposed with the sleeve, the trough being configured to receive bone replacing mass.

16. The endoprosthesis of claim 15, wherein the bone-replacing mass is porous and filled with prolonged action antibiotics.

17. The endoprosthesis of claim 16, wherein porous bone-replacing mass is made of hydroxyapatite ceramics.

* * * * *